(12) United States Patent
Lebok et al.

(10) Patent No.: US 10,589,133 B2
(45) Date of Patent: *Mar. 17, 2020

(54) COSMETIC PREPARATION AND USE THEREOF

(75) Inventors: Simona Lebok, Nuremberg (DE); Sigrid Hell, Georgensgmuend (DE); Marika Skultety, Erlangen (DE)

(73) Assignee: Schwan-STABILO Cosmetics GmbH & Co. KG, Heroldsberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/318,499

(22) PCT Filed: Feb. 2, 2011

(86) PCT No.: PCT/EP2011/000474
§ 371 (c)(1),
(2), (4) Date: Nov. 2, 2011

(87) PCT Pub. No.: WO2011/095331
PCT Pub. Date: Aug. 11, 2011

(65) Prior Publication Data
US 2012/0288462 A1    Nov. 15, 2012

(30) Foreign Application Priority Data
Feb. 2, 2010  (DE) .................... 20 2010 001 688 U

(51) Int. Cl.
| | | |
|---|---|---|
| *A61Q 1/06* | (2006.01) | |
| *A61Q 1/08* | (2006.01) | |
| *A61Q 1/10* | (2006.01) | |
| *A61K 8/891* | (2006.01) | |
| *A61K 8/81* | (2006.01) | |
| *A61K 8/02* | (2006.01) | |
| *A61K 8/86* | (2006.01) | |

(52) U.S. Cl.
CPC .............. *A61Q 1/10* (2013.01); *A61K 8/0229* (2013.01); *A61K 8/8111* (2013.01); *A61K 8/86* (2013.01); *A61K 8/891* (2013.01); *A61Q 1/06* (2013.01); *A61Q 1/08* (2013.01); *A61K 2800/872* (2013.01)

(58) Field of Classification Search
None
See application file for complete search history.

(56) References Cited

U.S. PATENT DOCUMENTS

| | | | | |
|---|---|---|---|---|
| 2,136,779 A | * | 11/1938 | Bednar ......................... | 132/218 |
| 4,769,234 A | * | 9/1988 | Pines et al. ................. | 424/172.1 |
| 5,407,958 A | * | 4/1995 | Heath et al. ................. | 514/546 |
| 6,719,966 B2 | * | 4/2004 | Abrutyn .................. | A61K 8/02 |
| | | | | 424/400 |
| 2003/0147837 A1 | * | 8/2003 | Cavazzuti ................ | A61K 8/37 |
| | | | | 424/70.17 |
| 2006/0019848 A1 | * | 1/2006 | Luo ......................... | A61K 8/064 |
| | | | | 510/130 |
| 2006/0067960 A1 | * | 3/2006 | Russ .................... | A61K 8/8194 |
| | | | | 424/401 |
| 2006/0134035 A1 | | 6/2006 | Zheng et al. | |
| 2006/0280763 A1 | | 12/2006 | Yoshida et al. | |
| 2007/0041922 A1 | * | 2/2007 | Reinhart et al. ............. | 424/70.7 |
| 2007/0212317 A1 | * | 9/2007 | Atis ...................... | A61K 8/8117 |
| | | | | 424/70.11 |
| 2008/0171006 A1 | | 7/2008 | Bui et al. | |
| 2008/0305067 A1 | | 12/2008 | Bui et al. | |
| 2009/0008026 A1 | * | 1/2009 | Kopf ........................ | C09J 7/045 |
| | | | | 156/187 |
| 2009/0047313 A1 | | 2/2009 | Bruechert et al. | |
| 2009/0092567 A1 | | 4/2009 | Chou et al. | |
| 2009/0257966 A1 | | 10/2009 | Schlossman et al. | |
| 2009/0317350 A1 | * | 12/2009 | Lu et al. ....................... | 424/70.7 |
| 2010/0061951 A1 | * | 3/2010 | Sujeeth et al. ............... | 424/70.7 |
| 2010/0254933 A1 | * | 10/2010 | Favre et al. ............... | 424/78.03 |
| 2012/0171137 A1 | * | 7/2012 | Bradsaw .................. | A61K 8/31 |
| | | | | 424/64 |
| 2013/0058883 A1 | * | 3/2013 | Kergosien ................ | A61K 8/31 |
| | | | | 424/70.7 |

FOREIGN PATENT DOCUMENTS

| | | | | |
|---|---|---|---|---|
| DE | 102007038936 A1 | | 2/2009 | |
| WO | WO9913016 | * | 3/1999 | .............. C09J 11/08 |
| WO | WO2009071675 | * | 6/2009 | .............. A61K 8/31 |

OTHER PUBLICATIONS

Dedraflow. https://www.in-cosmetics.com/_novadocuments/2342. Published Mar. 2009.*
Mascaras. http://www.specialchem4cosmetics.com/services/formulations-selector.aspx?type=14577. Published Jul. 12, 2009.*
Mascara Formulation. http://www.specialchem4cosmetics.com/formulations/guides/recipe.aspx?id=7. Published: May 5, 2006.*
Polyglyceryl-4 isostearate. http://www.paulaschoice.com/cosmetic-ingredient-dictionary/definition/polyglyceryl-4-isostearate. Published: Dec. 5, 2009.*
Dow Corning 5200 Formulation Aid. http://www2.dowcorning.com/DataFiles/090007b281d69d9e.pdf. Published Jul. 2013.*
Dow Corning SW-8005 C30 Resina Cerosa. http://www.cosmeticsonline.com.br/materia_prima/MP106_Daltomare%20-%208005%20(espanhol).pdf. Published Dec. 9, 2008.*
Sephora Jumbo Eye Pencil. http://www.makeupalley.com/product/showreview.asp/ItemId=33437/Jumbo-Eye-Pencil/Sephora-/Eyeliner. Published: Jan. 31, 2009.*
Dow Corning Product Information: SW-8005 C30 Resin Wax, Feb. 17, 2009.

* cited by examiner

*Primary Examiner* — Jyothsna A Venkat
(74) *Attorney, Agent, or Firm* — Bachman & LaPointe, PC

(57) ABSTRACT

A cosmetic preparation characterized by excellent adhesion at the place of application, comprises at least one silsesquioxane wax.

11 Claims, 1 Drawing Sheet

Experimental comparison and results

4% C30-45 Alkyldimethylsilyl Polypropylsilsesquioxane

↑ Fluid, no structure

4% Synthetic Wax Sephora formula

↑ Stick structure

COSMETIC PREPARATION AND USE THEREOF

BACKGROUND OF THE INVENTION

Figure 2:
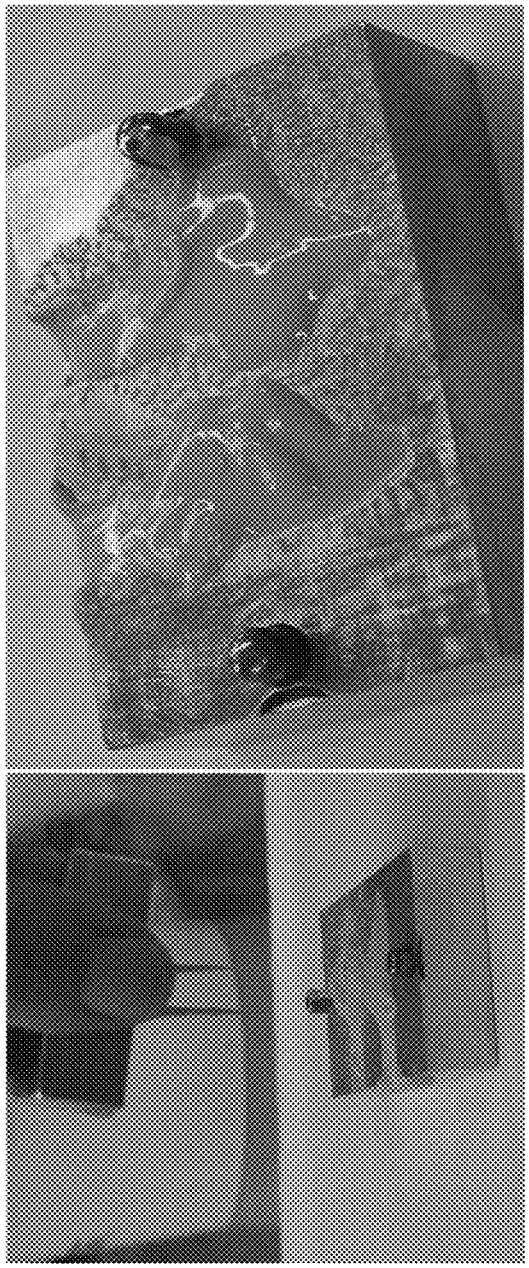
Figure 1:
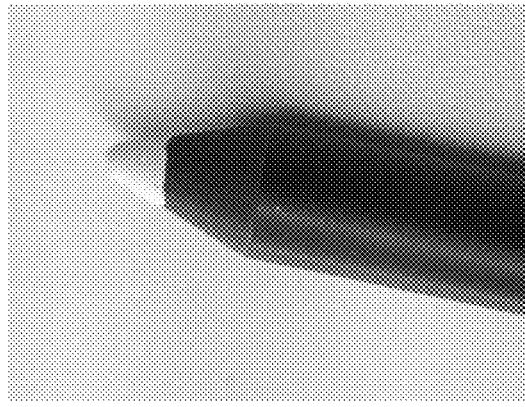

The invention concerns a cosmetic preparation and use thereof.

We can no longer imagine life nowadays without cosmetic products. The more fast-moving time becomes, the demands made on respective cosmetics are also becoming correspondingly higher. Whereas previously putting on makeup and caring for the skin and the body was enjoyed as a pleasure nowadays the requirement is to achieve a perfect appearance with as far as possible just one procedure. One consequence of this is products having a large number of ingredients which are intended to help deal with many skin defects at the same time and preferably just with a one-off application. While decorative effects of cosmetics can be immediately visualized in that respect the long-term effect of the products is achieved by active ingredients.

So that the advantageous effects of cosmetic preparations can also be durably achieved the cosmetic products must enjoy excellent adhesion to the place of application, that is to say for example the skin and its skin appendages, hair, mucous membranes and semi-mucous membranes. It is equally important that the products are water-resistant and are not transferred onto articles or parts of the skin as well as textiles with which they come into contact, which is popularly referred to as the "no transfer effect".

Commercially available cosmetic products which are both water-resistant and also have a no transfer effect are generally obtained by adding to ordinary wax mixtures, volatile silicone compounds which keep the wax preparation supple and malleable upon application and which after evaporation leave the film of wax behind on the area of application. A disadvantage in this respect is that the resulting "dried-off" wax film is often brittle or cracky due to the loss of the compounding, silicone-bearing solubilization agent, and has a matt, dull surface which tightens or burns at the place of application and leaves behind an unpleasant feel during the time it is worn. To overcome that disadvantage a proportion of lipophilic oils which are intended to keep the wax structure flexible is added to those purely wax-based preparations. A disadvantage here however is that it is precisely those oils, which remain on the skin, that preferably migrate due to capillary effects away from the place of application, which markedly reduces adhesion of the preparation at the place of application and leads to secondary effects such as the preparation running out onto surrounding areas of skin or hair, the so-called "bleeding-out" effect, which is intolerable in particular in the case of colored preparations.

As alternatives to silicone-bearing wax cosmetics, water-based cosmetic products on an emulsion or suspension base are offered, the durability and maintenance of which on the area of application is afforded by specific polymeric ingredients. After evaporation of the solvent those polymers form an at least partially water-resistant film which, depending on the respective polymer used, has a more or less pronounced gloss. A disadvantage of such water-based systems is that they require surfactants and/or emulsifiers in any case so that the water-bearing product is stable and can be distributed on the skin and does not drip or bead therefrom. Those surfactants and/or emulsifiers however have a detrimental effect on water resistance and mechanical resistance of the cosmetic film formed, for example upon contact with water or other protic solvents the film already formed re-emulsifies or solubilizes and detaches from the place of application or tears away. A further disadvantage is that large amounts of polymer are required to produce a durable polymer film. That also results in unpleasant tightening of the film at the place of application. That can only be partially counteracted by the addition of small molecules, so-called plasticizers, which however are often incompatible with the remaining constituents of the preparation.

The object of the present invention is thus to overcome the above-described disadvantages of known cosmetic products and to provide a cosmetic preparation which has excellent wearing properties, in particular adheres to the place of application for a long time, does not migrate therefrom or is not transferred, is water- and wipe-resistant and in addition is easy to apply uniformly. In addition the invention seeks to provide that the preparation is also storage-stable even at elevated or very low temperatures and withstands usual mechanical stresses as can act on current cosmetic products. In that respect the expression "storage-stable" is used to mean that the preparation according to the invention does not experience any noticeable change either visually or in sensory terms upon storage over a four-week period at between $-10°$ C. and $45°$ C.

SUMMARY OF THE INVENTION

The specified objects are attained by a cosmetic preparation which contains at least one silsesquioxane wax.

DETAILED DESCRIPTION

The subject-matter of the invention is a cosmetic preparation which contains at least one silsesquioxane wax of the formula $(R_2R'SiO_{1/2})_x(R''SiO_{3/2})_y$, and at least one thermoplast having at least one unit derived from cyclopentadiene. In the above-indicated formula in each case R is an alkyl group having between 1 and 8 C-atoms, R' is a monovalent alkyl group having between 9 and 46 C-atoms, R" is a monovalent alkyl group having between 1 and 8 C-atoms or an aryl group, wherein x and y can assume values of between 0.05 and 0.95. Besides the above-mentioned groups the silsesquioxane wax can also have further siloxy units such as for example $(R^1{}_3SiO_{1/2})_a$, $(R^2{}_2SiO_{2/2})_b$, $(R^3SiO_{3/2})_c$ or $(SiO_{4/2})_d$, which can also be referred to as M-, D-, T- and Q-units and are generally known. The described silsesquioxane wax is soluble or at least homogenously distributable in current wax or oil mixtures and acts as a structurant in the surrounding mass. Due to its structure it is capable of setting in the cosmetic preparation a matrix serving as a structurant framework in which the other components are embedded or at least added thereon. The silsesquioxane wax is made up of two different specific silicone-bearing units which impart to the wax both wax-like and also resin-like properties. Because of the $(R''SiO_{3/2})_y$-unit the molecule not only extends in the longitudinal direction in the preparation but has partially crosslinked regions which additionally stabilize the preparation. In that case, with the length of the residues R, R' or R" the wax-like character increases and the wax gains in lipophilia and substantivity. The melting range of the wax also increases therewith. The partially lipophilic character of the wax means that it can be well distributed in particular on skin and skin appendages, and also on mucous membranes and semi-mucous membranes, and for that purpose has a high level of adhesion so that the cosmetic preparation adheres well and long to the place of application and is also resistant to water. The resin-like character also promotes the long durability on the place of application, precisely due to the formation of the above-described matrix effect. In addition however the no transfer properties of the preparation are also promoted thereby. Without being bound down to a theory it is assumed that, due to the applied matrix, the components further contained in the cosmetic preparation are embedded therein so well that the silsesquioxane wax seemingly places a kind of protective film around the components, from which they cannot migrate. As a result the preparation after application is not transferred onto articles, skin or hair parts or textiles such as clothing, serviettes and the like, with which it comes into contact. The preparation according to the invention thus durably remains at the place of application.

The silicone-bearing unit first referred to in the foregoing formula has three residues, of which two can be the same. That structure unit forms the terminal unit of the base structure of the silsesquioxane wax. R' is a monovalent hydrocarbon residue having between 9 and 46 C-atoms in the base structure. The longer that residue is, the correspondingly greater is the lipophilia of the molecule and thus for example adhesion to skin, skin parts, mucous membranes and the like. In addition, with an increasing chain length of the residue R', there is an increase in compatibility in current lipophilic cosmetic raw materials, which markedly increases the stability of the overall preparation, in particular at high or extremely low temperatures. A chain length of more than 46 C-atoms in contrast however leads to severe stresses in the molecule so that its stability does not stand up under mechanical loading as occurs for example when a preparation is applied to an area of skin. The preparation has a brittle effect and crumbles. A hydrocarbon residue having at least 9 C-atoms is however required to afford the desired lipophilia. The residues identified by R can each be the same or different but they are preferably the same. R is in each case a straight-chain or branched hydrocarbon residue having between 1 and 8 carbons in its base structure. The greater the chain length of that second hydrocarbon residue R, the correspondingly more stressed is the molecule at its ends so that the chains of the residue R are partially superimposed with those of the residue R' or have a steric influence, which in spite of the chemical similarity can lead to steric inner-molecular stresses. In addition large residues R rather lead to partial blocking of the cavities which are opened by the silsesquioxane and which are actually available for the other components of the preparation. The chain length of the residue R should therefore not exceed 8 C-atoms. The unit last-mentioned in the foregoing formula not only forms the linear base structure of the silsesquioxane wax but is also a crosslinking structural element which imparts a resin-like character to the wax and therefore enhances the no transfer properties of the preparation according to the invention. It includes a siloxane unit with the residue R'' which can be an aryl residue or a monovalent hydrocarbon residue having between 1 and 8 C-atoms. Here too it is important that the molecule size or chain length of the residue R'' is not too great as otherwise the lattice-like structure afforded by the silsesquioxane wax is partially destroyed or filled by the residue R'' and therefore it can no longer serve as a support of the cosmetic preparation according to the invention. Particularly in the case of condensed ring systems or aryl groups with protruding sterically shielding substituents or an alkyl residue with a chain length of more than 8 C-atoms the probability of the stresses triggered by sterically conditioned repulsive interactions is so great that the structure matrix is expanded and can thus not be loaded. Preferred chain lengths for the residue R'' are between 3 and 6 C-atoms or however R'' is a phenyl group with or without substituents. It has been found that then the interactions with the primary unit are so slight that the usual cosmetic components are homogenously and stably embedded in the structure of the silsesquioxane wax and are durably stabilized therein.

The amounts of the silsesquioxane wax used are not restricted in detail terms. It is preferred however if the amount is between 1 and 20% by weight and particularly preferably between 3 and 15% by weight with respect to the total weight of the preparation. With amounts of less than 1% by weight the advantageous desirable properties of the preparation according to the invention such as long adhesion at the place of application or the no transfer properties as well as the preparation-stabling effect are achieved in less pronounced fashion. Amounts which exceed 20% by weight with respect to the total weight of the preparation of the invention are admittedly possible but they no longer cause a marked increase in the advantageous properties of the preparation according to the invention.

As in the case of other long-chain hydrocarbon waxes, that is to say for example high-melting ozocerites, microcrystalline waxes and paraffins, or crosslinking resins such as polyurethane polymers or other functional acrylate polymers, the above-described silsesquioxane wax however, due to its partial crystallinity, also has properties which have a less advantageous effect on durability, or stated in better terms, the overall appearance of the applied preparation. Thus it was found that on its own it is not sufficient to add the above-mentioned silsesquioxane wax to a usual wax mixture to improve durability at the place of application, for that also promotes brittleness and cracking of the surrounded wax material as the elastic proportion in the silsesquioxane wax is less.

It was now surprisingly found that a cosmetic preparation which contains the described silsesquioxane wax in combination with a thermoplast with at least one unit derived from cyclopentadiene has excellent durable adhesion at the area of application and is extremely water-resistant and wipe-resistant. In addition the preparation is not transferred onto articles, textiles or skin or hair parts with which it comes into contact. The preparation can be easily applied and forms a very fine homogenous film which does not transfer or which does not migrate from the location of application and which is nonetheless supple and pleasantly soft. Equally the tendency to migration is reduced by the combination of components according to the invention and the preparation even withstands capillary effects as act in fine skin wrinkles. What is astonishing is that it is precisely the combination of silsesquioxane wax with a thermoplast with at least one unit derived from cyclopentadiene that imparts adequate suppleness to a wax-like preparation which otherwise tends to be brittle, so that the film formed after application remains elastic on the surface to which it was applied so that breaking up in skin wrinkles or skin irregularities and other film defects are prevented. The application surface remains uniformly covered over a long period of time without drying out or producing an unpleasant tightening feel or even burning.

A thermoplast in accordance with the invention is a plastic material which can be deformed easily and without being destroyed (that is to say thermoplastically) in a given temperature range. That process is reversible, which means that it can be repeated as often as may be desired by cooling and re-heating to the molten state, as long as so-called thermal decomposition of the thermoplast does not occur due to overheating. Thermoplasts are made up of carbon chains which are slightly or not branched, therefore predominantly straight-chain, which are joined together only by weak physical bonds. In addition thermoplasts can also have partially crystalline regions. The carbon chains are predominantly oriented parallel in those regions.

According to the invention, thermoplasts are used which have at least one unit derived from cyclopentadiene. The unit derived from cyclopentadiene can be cyclopentadiene, dicyclopentadiene, polycyclopentadiene, polydicyclopentadiene or a hydrogenated derivative of one of said units. The thermoplast can comprise only one of those units or a mixture of units or can be made up from cyclopentadiene units and other monomers. Thus the thermoplast can be a homopolymer, copolymer, terpolymer, crosspolymer or the like.

Without being bound down to a theory it is assumed that the unit derived from cyclopentadiene is particularly well embedded in the matrix afforded by the silsesquioxane wax according to the invention or as a less sterically demanding molecule scarcely produces repulsive interactions in the matrix structure. It serves equally as a spacer and also as a filling substance in the cavities of the wax structure. Seemingly by virtue of their structure both raw materials cooperate in such an optimum fashion that a certain elasticity is imparted to the overall assembly of the preparation due to the thermoplast insofar as the unit derived from cyclopentadiene partially expands the rigid alkyl siloxane structure and thus makes it pliable and smooth. As the thermoplasts according to the invention also enhance adhesion to skin, skin appendages, mucous membranes and the like by virtue of their lipophilia which is in particular also afforded by the molecule derived from cyclopentadiene both components according to the invention cooperate synergistically in regard to durability on the place of application, and that imparts to the preparation according to the invention outstandingly long adhesion as well as an extremely good no transfer effect.

The thermoplasts are not limited in detail terms. They must however have at least one unit derived from cyclopentadiene and should be suitable for cosmetic applications. The larger the proportion of units derived from cyclopentadiene, the correspondingly more pronounced are the positive properties on the overall preparation which contain the silsesquioxane wax according to the invention.

The thermoplast or the mixture of thermoplasts can be used in any amounts. It is advantageous however if the amount of thermoplast is between 2 and 20% by weight, preferably between 5 and 12% by weight, with respect to the total weight of the composition. With a content of less than 2% by weight in relation to the overall composition the effect of promoting elasticity and adhesion cannot be achieved to an increased degree, in the preparation. With a content as from 20% by weight with respect to the total weight of the preparation in addition it is not possible to achieve any further improvements in regard to adhesion at the place of application.

The combination of the thermoplast as described hereinbefore with a silsesquioxane wax in accordance with the aforementioned formula has proven to be particularly good for the cosmetic preparation according to the invention, if in the formula R respectively denotes a methyl group, R' denotes an alkyl group having 30 to 46 C-atoms and R" denotes an alkyl group having 3 C-atoms. It has been found here that the relationship of the lengths of the alkyl groups is balanced out in such a way that an optimum structural configuration is formed, which promotes the adhesion durability of the preparation according to the invention to the place of application. It is assumed that on the one hand the matrix afforded by the silsesquioxane wax is just of such a wide mesh that the thermoplast which is essential to the invention and the usual cosmetic raw material components are sufficiently stabilized therein so that they do not migrate out of the preparation or suffer transfer, but on the other hand the matrix is of such a fine mesh that as a result the preparation experiences a sufficient stabilizing effect. In particular the long-adhering properties of the preparation and the no transfer properties are particularly greatly pronounced in this embodiment. It is assumed that the thermoplast carrying at least one unit derived from cyclopentadiene can here particularly well sink into the structure and the cavities of the matrix afforded by the silsesquioxane wax so that the elasticity of the overall structure is extraordinarily increased so that the preparation is not only easy to apply but in addition also adheres to the place of application for a long time and forms a regular film which even after being worn for a long period neither burns nor leads to a tightening skin sensation, but remains pleasantly soft and supple.

Preferred thermoplasts are those which are selected from the list hereinafter, the thermoplasts being specified with their INCI (International Nomenclature of Cosmetic Ingredients) names: dicyclopentadiene/t-butylcresol copolymer, dicyclopentadiene/isopentene/isoprene copolymer, dicyclopentadiene/isopentene/isoprene/styrene copolymer, hydrogenated dicyclopentadiene/isopentene/isoprene copolymer, hydrogenated dicyclopentadiene/isopentene/isoprene/styrene copolymer, hydrogenated polycyclopentadiene, hydrogenated polydicyclopentadiene and polycyclopentadiene or mixtures thereof, hydrogenated polydicyclopentadiene being particularly preferred. Using copolymers, that is to say thermoplasts with other monomer units than units derived from cyclopentadiene means that the structural properties of the overall structure in the cosmetic preparation according to the invention can be adjusted in specifically targeted fashion. That also influences the physical properties of the preparation such as melting characteristics, viscosity, toughness, brittleness and the like. The man skilled in the art can set the desired properties by simple routine tests. It will be noted however that it is essential, for the same reasons as mentioned hereinbefore, for the unit derived from cyclopentadiene to be present. Of the above-mentioned list, hydrogenated polydicyclopentadiene has proven to be a particularly effective thermoplast for promoting the elasticity of the preparation. It is assumed that this is to be attributed to the highly regular structure. The durability of the preparation according to the invention at the place of application and in particular resistance to wiping and the no transfer characteristic could be particularly greatly increased in that way without causing a lack of elasticity and at the same time strength of the preparation.

The preparation according to the invention can be in the form of an emulsion, a wax and/or oil and/or silicone mixture or in the form of a dispersion. The positive properties of the preparation according to the invention are particularly clearly apparent when it is water-free. Admittedly the combination of silsesquioxane wax and thermoplast, that is essential to the invention, stabilizes any kind of cosmetic preparation, that is to say also W/O emulsions, O/W emulsions or multiple emulsions, but it will be noted that the water-resistance and resistance to wiping is once again markedly increased in water-free preparations.

The no transfer properties of the cosmetic preparation according to the invention can be further increased by the addition of components which are volatile at ambient temperature. In principle, any component which is volatile at ambient temperature can be considered for the preparation according to the invention. The higher the vapor pressure of the volatile component, the more rapidly it evaporates after application and leaves behind the other, non-volatile components of the cosmetic preparation at the place of application, which then form the long-adhering film. Suitable volatile components can be selected from the group consisting of: cyclic polydimethylsiloxanes such as for example cyclotetrasiloxane, cyclopentasiloxane, cyclohexasiloxane and other volatile straight-chain polydimethylsiloxanes, also called methicones or dimethicones, volatile hydrocarbons having between 5 and 16 C-atoms such as for example: isododecane or isohexadecane, or mixtures thereof. Further suitable volatile raw materials are also polymeric compounds such as those which are available under the INCI (International Nomenclature of Cosmetic Ingredients) polydecenes, polyisobutenes, hydrogenated polyisobutenes or hydrogenated poly(C6-14 olefin), or mixtures thereof, as long as those compounds or mixtures are volatile at ambient temperature. The specified raw materials have a good evaporation rate at ambient temperature but are also not too volatile so that the cosmetic preparation according to the invention remains applicable for a sufficiently long time. No particular limits are set in regard to the amount of the volatile component. The amount of volatile component can be easily determined by the man skilled in the art in dependence on the desired form of application and the application properties.

Preferably the cosmetic preparation according to the invention includes at least one hydrogenated polymeric hydrocarbon. They can have both a straight-chain and also a branched structure. Hydrogenated polymeric hydrocarbons have a high adhesive to the skin and thus generally improve the application properties of cosmetic preparations intended for the skin or mucous membranes. It has surprisingly been found however that hydrogenated polymeric hydrocarbons also increased the elasticity and gloss of the cosmetic preparation according to the invention. It is assumed that those hydrocarbons can function as a binding member between the alkyl silsesquioxane units and by virtue of their high affinity to the thermoplast which is essential according to the invention do not disturbingly intervene in the structural configuration but rather further enhance the stability thereof, more specifically by intermolecular interactions. As a result the adhesion of the preparation on the skin is also increased, whereby the no transfer characteristic is also retained over a long period. The film formed adheres in stable fashion at the place of application, it does not become brittle and it does not split but clings uniformly to the surface of the area of application.

Particularly suitable hydrogenated polymeric hydrocarbons are in that respect selected from the group consisting of: polyisobutene, polydecene, polyolefins having units which include between 6 and 14 C-atoms, polybutene, polyethylene, polystyrene, polyisoprene, copolymers, terpolymers or cross-polymers or mixtures thereof, wherein the respective compounds can also be partially or fully hydrogenated. It is known to the man skilled in the art in that respect, which monomers or polymers he can combine together to promote desired properties of the cosmetic preparation.

The amount of hydrogenated polymeric hydrocarbons is not limited in detail terms and can be easily determined by the man skilled in the art in dependence on the desired application profile.

Furthermore the cosmetic preparation according to the invention preferably also includes at least one polyglyceryl ester with between 3 and 10 glyceryl units. Polyglyceryl esters are normally employed as emulsifiers in cosmetic preparations. It will be noted that it has been found in the cosmetic preparation according to the invention that the use of at least one polyglyceryl ester promotes the texture and in particular color homogeneity and color intensity. Admittedly the components of the cosmetic preparation are already uniformly embedded in the structure of the preparation by virtue of the matrix afforded by the raw material combination which is essential to the invention, but it has been found that using at least one polyglyceryl ester with between 3 and 10 glyceryl units, when wetting in particular filling substances, pigments and other part-polar components, means that the uniform distribution thereof can be even more markedly increased. That effect is particularly markedly apparent precisely in relation to pigmented preparations. It appears here as though the glyceryl ester serves as an anchor to hold the pigment or the dye both in the matrix and also on the surface thereof. In that way the pigments and dyes interact particularly well with the light incident thereon and exhibit an intensive color spectrum. For that so-called "anchor effect", it is necessary for the glyceryl ester to have at least three glyceryl units so that there are also sufficiently polar units for them to be taken up by pigments, filler substances and the like. In contrast, with glyceryl esters having more than 10 glyceryl units it is difficult to obtain stable preparations as in the case of those compounds the emulsifying character appears to be in the foreground, which interferes with the matrix structure of the silsesquioxane wax so that the desired levels of storage stability are not achieved.

The amount of polyglyceryl ester is not limited in detail terms and can be easily determined by the man skilled in the art in dependence on the desired application profile.

The glyceryl esters are not limited in detail terms. Glyceryl esters which are selected from the list hereinafter have proven to be particularly advantageous, the glyceryl esters being specified with their INCI (International Nomenclature of Cosmetic Ingredients) names: apricot stone oil polyglyceryl-6 ester, apricot stone oil polyglyceryl-10 ester, babassu oil polyglyceryl-4 esters, babassu oil polyglyceryl-6 ester, bis-butyldimethicone polyglyceryl-3, borage seed oil polyglyceryl-6 ester, candelilla/jojoba/rice husks polyglyceryl-3 ester, cocoa butter polyglyceryl-6 ester, coconut oil polyglyceryl-6 ester, coffee bean oil polyglyceryl-6 ester, diisostearoyl polyglyceryl-3 dimer dilinoleate, glyceryl/polyglyceryl-6 isostearate/behenate ester, isopolyglyceryl-3 dimethicone, isopolyglyceryl-3 dimethiconol, lauryl polyglyceryl-6 cetearyl glycol ether, macadamia seed oil polyglyceryl-6 ester behenate, olive oil polyglyceryl-4 ester, olive oil polyglyceryl-6 ester, polyglyceryl-3 beeswax, polyglyceryl-6 behenate, polyglyceryl-10 behenate/eicosadioate, polyglyceryl-8 C12-20 acid ester, polyglyceryl-3 caprate, polyglyceryl-4 caprate, polyglyceryl-5 caprate, polyglyceryl-6 caprate, polyglyceryl-10 caprate, polyglyceryl-3 caprylate, polyglyceryl-4 caprylate, polyglyceryl-6 caprylate, polyglyceryl-10 caprylate, polyglyceryl-3 cocoate, polyglyceryl-4 cocoate, polyglyceryl-8 decaerucate/decaisostearate/decaricinoleate, polyglyceryl-10 decaethylhexanoate, polyglyceryl-10 decahydroxystearate, polyglyceryl-10 decaisostearate, polyglyceryl-10 decastearate, polyglyceryl-3 dicaprate, polyglyceryl-3 diisostearate, polyglyceryl-6 diisostearate, polyglyceryl-10 diisostearate, polyglyceryl-4 dilaurate, polyglyceryl-5 dilaurate, polyglyceryl-10 dimyristate, polyglyceryl-3 dioleate, polyglyceryl-5 dioleate, polyglyceryl-6 dioleate, polyglyceryl-10 dioleate, polyglyceryl-6 dipalmitate, polyglyceryl-10 dipalmitate, polyglyceryl-3 disiloxane dimethicone, polyglyceryl-3 distearate, polyglyceryl-10 hexaerucate, polyglyceryl-10 hexaisostearate, polyglyceryl-6 hexaoleate, polyglyceryl-10 hexaoleate, polyglyceryl-5 hexastearate, polyglyceryl-3 isostearate, polyglyceryl-4 isostearate, polyglyceryl-5 isostearate, polyglyceryl-6 isostearate, polyglyceryl-4 isostearate/laurate, polyglyceryl-3/lauryl polydimethylsiloxyethyl dimethicone crosspolymer, polyglyceryl-10 linoleate, polyglyceryl-3 methyl glucose distearate, polyglyceryl-3 myristate, polyglyceryl-5 myristate, polyglyceryl-3 oleate, polyglyceryl-4 oleate, polyglyceryl-10 oleate, polyglyceryl-3 palmitate, polyglyceryl-6 palmitate, polyglyceryl-10 palmitate, polyglyceryl-10 pentaisostearate, polyglyceryl-10 pentalaurate, polyglyceryl-5 pentamyristate, polyglyceryl-3 pentaricinoleate, polyglyceryl-6 pentaricinoleate, polyglyceryl-4 pentastearate, polyglyceryl-6 pentastearate, polyglyceryl-3 polydimethylsiloxyethyl dimethicone, polyglyceryl-6 polyhydroxystearate, polyglyceryl-4 diisostearate/polyhydroxystearate/sebacate, polyglyceryl-3 polyricinoleate, polyglyceryl-4 polyricinoleate, polyglyceryl-6 sesquiisostearate, polyglyceryl-6 sesquistearate, polyglyceryl-3 stearate, polyglyceryl-4 stearate, polyglyceryl-6 tetrabehenate, polyglyceryl-6 tetracaprylate, polyglyceryl-5 tribehenate, polyglyceryl-3 triisostearate, polyglyceryl-5 trimyristate, polyglyceryl-4 tristearate, polyglyceryl-5 tristearate, thistle oil polyglyceryl-6 ester, sesame oil polyglyceryl-6 ester, shea butter polyglyceryl-6 ester, soya bean oil polyglyceryl-6 ester, sunflower seed oil polyglyceryl-6 ester or mixtures thereof.

The preparation according to the invention can preferably also include filler substances such as for example polymethylsilsesquioxane, dimethicone/vinyldimethicone crosspolymer, dimethicone/bis-isobutyl PPG-20 crosspolymer, dimethicone crosspolymer, mica, silica, nylon-12, PMMA, boron nitride, polyethylene, HDI/trimethylol hexyllactone crosspolymer, magnesium stearate, zinc oxide or mixtures thereof (the foregoing designations in accordance with INCI—International Nomenclature of Cosmetic Ingredients). The application profile of the preparation may be varied from smoothly sliding to dryly matt by means of those fillers. Common filler substances are known to the man skilled in the art, but the above-mentioned have proven to be most compatible with the preparation according to the invention so that it is precisely the long-term stability at elevated and also at low temperature that is not detrimentally influenced. Thus the preparations according to the invention are stable at temperatures of between −10° C. and 45° C. over four weeks, that is to say after storage it is not possible to detect either visually or by sensory means differences in relation to the corresponding non-stressed preparations.

The amount of filler substance is not limited in detail terms and can be easily determined by the man skilled in the art in dependence on the desired application profile.

It is further advantageous if the preparation contains so-called film-forming agents. Film-forming agents in accordance with the invention are those compounds which have a certain adhesion to area of application, such as for example the skin, and there contribute to stabilizing the preparation according to the invention on the surface of the skin. In that way the adhesion of the preparation to the skin is increased, in particular the long-term adhesion of the preparation. The no transfer characteristic of the preparation is also increased by the addition of film-forming agents. The preparation according to the invention is therewith fixed at the place of application even longer, that is to say over several hours up to a day, without migrating therefrom or without suffering transfer. Preferably the film-forming agents in accordance with the invention are selected from polymers which are known for those purposes such as polyurethane polymers, acrylic acid or acrylate-based polymers, silicone-based polymers, copolymers or crosspolymers thereof, as well as mixtures thereof. The film-forming agents can be used in the amounts usually employed, which the man skilled in the art can easily establish by routine tests. A polymer which is listed under the INCI as acrylates/dimethicone copolymer has proven to be a particularly suitable film-forming agent. It can be easily and homogenously incorporated into the preparation according to the invention and after evaporation of all volatile components forms at the place of application a stable but elastic film which is stable over several hours, which does not crack and which durably confines the components contained in the preparation so that "bleeding-out" or migration of individual components is prevented. The no transfer effect of that preparation according to the invention is markedly enhanced.

The cosmetic preparation according to the invention can also contain further current components suitable for cosmetic preparations such as for example pigments, dyestuffs, antioxidants, preservation substances, fragrances, buffers, oils, plasticisers, care substances and others which are used in the usual amounts.

In addition the cosmetic preparation according to the invention can be in liquid, semi-solid, that is to say creamy or pasty, or solid form, and after filling in suitable application vessels, can be easily taken therefrom again. It has been found that the particular wearing properties can be implemented not only in pasty or liquid preparations but also in solid materials which can be shaped to form sticks which can then be offered as cosmetic pencils. Cosmetic pencils have the advantage in that respect that they are easy to manage and can be easily employed at any time. The preparation according to the invention, in solid form, can be mechanically loaded in such a way that sticks can be shaped therefrom, which even have sufficient strength that they can be used in free-standing relationship in rotational mechanisms.

Processes for the production of sticks are well-known to the man skilled in the art and the known processes are suitable for the processing of the materials according to the invention. Thus the preparation according to the invention can be shaped by casting or by shaping the material by means of the application of pressure. The sticks produced can either be used in rotational mechanisms or they can be processed to form pencils, for example wood pencils. It is equally possible for the material to be cast directly into a mechanism or a casing for a pencil. By virtue of their good properties the sticks formed from the material according to the invention can occur in many different forms, in which case the stick diameter can be adjusted according to the respective area of use involved. Suitable stick diameters range between 1 and 20 mm, preferably 3 and 10 mm.

As a further advantage of the preparation according to the invention it has been found that it can be particularly well shaped to afford free-standing sticks which enjoy excellent stability, that is to say resistance to fracture, storage stability, stability in respect of use and the like, without the stability thereof having a detrimental effect on the application properties. Free-standing sticks which are mostly used in rotational mechanisms to afford an applicatable stick are normally particularly susceptible in regard to mechanical loadings. Because of their stable internal structure however the preparation according to the invention has excellent stability and can therefore be particularly well used for the production of free-standing sticks.

The preparation according to the invention is particularly suitable for the production of a cosmetic pencil. Such a cosmetic pencil can be an eyeliner, eyeshadow, eyebrow pencil, lipliner, lipstick, mascara, tattoo, blusher or a concealer material such as a concealer pencil.

EXAMPLES

Unless otherwise stated the amounts specified in respect of the individual components relate to percent by weight in relation to the total weight of the composition.

Unless otherwise stated the individual components are specified with their INCI (International Nomenclature of Cosmetic Ingredients).

Example 1

Eyeliner in Pencil Form

| Components | % by weight |
|---|---|
| Polyethylene | 13 |
| Synthetic wax | 8 |
| Hydrogenated polydicyclopentadiene | 7 |
| Polyglyceryl-10 pentaisostearate | 3 |
| C30-45 alkyldimethylsilyl polypropylsilsesquioxane | 6 |
| Antioxidant | 0.2 |
| Polymethyl methacrylate | 5 |
| Isoparaffin | 22.8 |
| Pigments | 35 |

Preparation:

All components except for the isoparaffin and the pigments were melted with stirring in a suitable container until homogenous. The pigments were then added and the material homogenized. Then the pigment-bearing material was melted again, the isoparaffin was added and the material was cast hot into a suitable pencil mold.

After cooling a stick of a diameter of 4 mm could be taken from the mold, and could be inserted into a suitable mechanism.

The material was distinguished by a pleasantly soft and smooth, slightly creamy application at the upper and also lower eyelid. Color distribution was homogenous.

The preparation adhered at the place of application for more than 8 hours and was not transferred onto the upper eyelid.

The preparation was also water-resistant, that is to say after drying and after subsequent rinsing of the applied area with warm water at 40° C. for 10 minutes it was not possible visually with the naked eye to see any change in the applied preparation.

In addition when the pencil was stored over 4 weeks at −10° C., 45° C. and in comparison therewith at 25° C. (ambient temperature), it was not possible to observe any change in relation to corresponding non-stressed pencils either visually or in sensory terms.

Example 2

Lipstick

| Component | % by weight |
|---|---|
| Candelilla wax | 10 |
| Polyethylene | 6 |
| Hydrogenated polydicyclopentadiene | 7.5 |
| C30-45 alkyldimethylsilyl polypropylsilsesquioxane | 7.5 |
| Antioxidant | 0.3 |
| Polyglyceryl-4 diisostearate/polyhydroxystearate | 4.2 |
| Acrylates/dimethicone copolymer | 5 |
| Dimethicone | 11.3 |
| Polybutene | 6.2 |
| Isododecane | 15.1 |
| Shea butter | 0.8 |
| Pigments | 22 |
| Polymethylsilsesquioxane | 4.1 |

Preparation:

All components except for the isododecane and the pigments were melted with stirring in a suitable container until homogenous. The pigments were then added and the material homogenized. Then the pigment-bearing material was melted again, the isododecane was added and the material was cast hot into a suitable pencil mold.

After cooling a stick of a diameter of 8 mm could be taken from the mold, and could be inserted into a suitable lipstick mechanism.

The material was distinguished by a light, creamy application and could be distributed smoothly on the lips. Color distribution was homogenous and concealing. The preparation adhered at the place of application for more than 8 hours and was not transferred onto cigarettes, cups, handkerchiefs or parts of the skin, that come into contact with the lips.

The preparation was also water-resistant, that is to say after drying and after subsequent rinsing of the applied area with warm water at 40° C. for 10 minutes it was not possible visually with the naked eye to see any change in the applied preparation.

In addition when the pencil was stored over 4 weeks at −10° C., 45° C. and in comparison therewith at 25° C. (ambient temperature), it was not possible to observe any change in relation to corresponding non-stressed pencils either visually or in sensory terms.

Example 3

Eyeshadow

| Components | % by weight |
|---|---|
| Stearyl dimethicone | 9 |
| Polyethylene | 8.2 |
| C20-40 alcohols and polyethylene | 1.0 |
| Hydrogenated polydicyclopentadiene | 7.8 |
| C30-45 alkyldimethylsilyl polypropylsilsesquioxane | 10.6 |
| Antioxidant | 0.2 |
| Squalane | 6.0 |
| Microcrystalline wax | 2.0 |
| Hydrogenated polydecene | 4.4 |
| Hydrogenated polyisobutene | 4.3 |
| Isododecane | 20.9 |
| Hydrogenated (C6-14 olefin) polymers | 5.8 |
| Pigments/fillers | 17.6 |
| HDI/trimethylol hexyllactone crosspolymer | 2.2 |

Preparation:

All components except for the isododecane and the pigments were melted with stirring in a suitable container until homogenous. The pigments were then added and the material homogenized. Then the pigment-bearing material was melted again, the isododecane was added and the material was cast hot into a tube.

After cooling the material could be easily applied from the tube onto a finger or an application implement.

The material was distinguished by a light, smooth application and could be easily distributed on the eyelid without applying much pressure. Color distribution was homogenous and concealing. The preparation adhered at the place of application for more than 8 hours and was not transferred onto the other parts of the skin.

The preparation was also water-resistant, that is to say after drying and after subsequent rinsing of the applied area with warm water at 40° C. for 10 minutes it was not possible visually with the naked eye to see any change in the applied preparation.

In addition when the pencil was stored over 4 weeks at −10° C., 45° C. and in comparison therewith at 25° C. (ambient temperature), it was not possible to observe any change in relation to corresponding non-stressed pencils either visually or in sensory terms.

Example 4

Concealer

| Components | % by weight |
| --- | --- |
| Hydrogenated jojoba oil | 10.2 |
| Phenyl trimethicone | 4.5 |
| Polyglyceryl-3 diisostearate | 3.0 |
| Hydrogenated polycyclopentadiene | 4.0 |
| C30-45 alkyldimethylsilyl polypropylsilsesquioxane | 8.1 |
| Preservative | 0.8 |
| Hydrogenated polyisobutene | 3.3 |
| Dimethicone | 14.2 |
| Cyclopentasiloxane | 22.8 |
| Nylon-12 | 14.0 |
| Pigments | 8.1 |
| Silica | 2.2 |
| Boron nitride | 4.5 |
| Antioxidant | 0.3 |

Preparation:

All components except for the cyclopentasiloxane and the pigments were melted with stirring in a suitable container until homogenous. The pigments were then added and the material homogenized. Then the pigment-bearing material was melted again, the cyclopentasiloxane was added and the material was cast hot into a suitable pencil mold.

After cooling a stick of a diameter of 6 mm could be taken from the mold, which could be inserted into a suitable pencil mechanism.

The material was distinguished by a slightly powdery, dryly smooth application and could be distributed on the skin without applying much pressure. Color distribution was homogenous and semi-concealing. The preparation adhered at the place of application for more than 8 hours and was not transferred onto the other parts of the skin or textiles coming into contact therewith.

The preparation was also water-resistant, that is to say after drying and after subsequent rinsing of the applied area with warm water at 40° C. for 10 minutes it was not possible visually with the naked eye to see any change in the applied preparation.

In addition when the pencil was stored over 4 weeks at −10° C., 45° C. and in comparison therewith at 25° C. (ambient temperature), it was not possible to observe any change in relation to corresponding non-stressed pencils either visually or in sensory terms.

The invention claimed is:

1. A cosmetic preparation comprising:
at least one silsesquioxane wax of the formula:

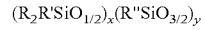

$(R_2R'SiO_{1/2})_x(R''SiO_{3/2})_y$ wherein R denotes an alkyl group having between 1 and 8 carbon atoms, R' denotes a monovalent alkyl group having between 9 and 46 carbon atoms, R" is a monovalent alkyl group having between 1 and 8 carbon atoms or an aryl group and wherein x and y can assume values of between 0.05 and 0.95; and
hydrogenated polydicyclopentadiene at least two components which are volatile at ambient temperature, wherein the volatile components are selected from the group consisting of: cyclotetrasiloxane, cyclopentasiloxane, cyclohexasiloxane, straight-chain polydimethylsiloxanes, isododecane, hydrogenated polyisobutene, hydrogenated polydecene, hydrogenated poly(C6-14 olefins), hydrogenated polybutene, hydrogenated polyethylene, hydrogenated polystyrene, hydrogenated polyisoprene, and mixtures thereof.

2. The cosmetic preparation as set forth in claim 1, wherein R is a methyl group, R' is an alkyl group having between 30 and 46 carbon atoms and R" is an alkyl group having 3 carbon atoms.

3. The cosmetic preparation as set forth in claim 1, wherein the preparation is water-free.

4. The cosmetic preparation as set forth in claim 1, wherein the preparation contains at least one polyglyceryl ester.

5. The cosmetic preparation as set forth in claim 4, wherein the polyglyceryl ester has between 3 and 10 glyceryl units.

6. The cosmetic preparation as set forth in claim 5, wherein the polyglyceryl ester is selected from the group consisting of:
apricot stone oil polyglyceryl-6 ester, apricot stone oil polyglyceryl-10 ester, babassu oil polyglyceryl-4 esters, babassu oil polyglyceryl-6 ester, bis-butyldimethicone polyglyceryl-3, borage seed oil polyglyceryl-6 ester, candelilla/jojoba/rice husks polyglyceryl-3 ester, cocoa butter polyglyceryl-6 ester, coconut oil polyglyceryl-6 ester, coffee bean oil polyglyceryl-6 ester, diisostearoyl polyglyceryl-3 dimer dilinoleate, glyceryl/polyglyceryl-6 isostearate/behenate ester, isopolyglyceryl-3 dimethicone, isopolyglyceryl-3 dimethiconol, lauryl polyglyceryl-6 cetearyl glycol ether, macadamia seed oil polyglyceryl-6 ester behenate, olive oil polyglyceryl-4 ester, olive oil polyglyceryl-6 ester, polyglyceryl-3 beeswax, polyglyceryl-6 behenate, polyglyceryl-10 behenate/eicosadioate, polyglyceryl-8 C12-20 acid ester, polyglyceryl-3 caprate, polyglyceryl-4 caprate, polyglyceryl-5 caprate, polyglyceryl-6 caprate, polyglyceryl-10 caprate, polyglyceryl-3 caprylate, polyglyceryl-4 caprylate, polyglyceryl-6 caprylate, polyglyceryl-10 caprylate, polyglyceryl-3 cocoate, polyglyceryl-4 cocoate, polyglyceryl-8 decaerucate/decaisostearate/decaricinoleate, polyglyceryl-10 decaethylhexanoate, polyglyceryl-10 decahydroxystearate, polyglyceryl-10 decaisostearate, polyglyceryl-10 decastearate, polyglyceryl-3 dicaprate, polyglyceryl-3 diisostearate, polyglyceryl-6 diisostearate, polyglyceryl-10 diisostearate, polyglyceryl-4 dilaurate, polyglyceryl-5 dilaurate, polyglyceryl-10 dimyristate, polyglyceryl-3 dioleate, polyglyceryl-5 dioleate, polyglyceryl-6 dioleate, polyglyceryl-10 dioleate, polyglyceryl-6 dipalmitate, polyglyceryl-10 dipalmitate, polyglyceryl-3 disiloxane dimethicone, polyglyceryl-3 distearate, polyglyceryl-10 hexaerucate, polyglyceryl-10 hexaisostearate, polyglyceryl-6 hexaoleate, polyglyceryl-10 hexaoleate, polyglyceryl-5 hexastearate, polyglyceryl-3 isostearate, polyglyceryl-4 isostearate, polyglyceryl-5 isostearate, polyglyceryl-6 isostearate, polyglyceryl-4 isostearate/laurate, polyglyceryl-3/lauryl polydimethylsiloxyethyl dimethicone crosspolymer, polyglyceryl-10 linoleate, polyglyceryl-3 methyl glucose distearate, polyglyceryl-3 myristate, polyglyceryl-5 myristate, polyglyceryl-3 oleate, polyglyceryl-4 oleate, polyglyceryl-10 oleate, polyglyceryl-3 palmitate, polyglyceryl-6 palmitate, polyglyceryl-10 palmitate, polyglyceryl-10 pentaisostearate, polyglyceryl-10 pentalaurate, polyglyceryl-5 pentamyristate, polyglyceryl-3 pentaricinoleate, polyglyceryl-6 pentaricinoleate, polyglyceryl-4 pentastearate, polyglyceryl-6 pentastearate, polyglyceryl-3 polydimethylsiloxyethyl dimethicone, polyglyceryl-6 polyhydroxystearate, polyglyceryl-4 diisostearate/polyhydroxystearate/sebacate, polyglyceryl-3 polyricinoleate, polyglyceryl-4 polyricinoleate, polyglyceryl-6 sesquiisostearate, polyglyceryl-6 sesquistearate, polyglyceryl-3 stearate, polyglyceryl-4 stearate, polyglyceryl-6 tetrabehenate, polyglyceryl-6 tetracaprylate, polyglyceryl-5 tribehenate, polyglyceryl-3 triisostearate, polyglyceryl-5 trimyristate, polyglyceryl-4 tristearate, polyglyceryl-5 tristearate, thistle oil polyglyceryl-6 ester, sesame oil polyglyceryl-6 ester, shea butter polyglyceryl-6 ester, soya bean oil polyglyceryl-6 ester, sunflower seed oil polyglyceryl-6 ester, and mixtures thereof.

7. The cosmetic preparation as set forth in claim 6, wherein the preparation contains at least one filler selected from the group consisting of:
polymethylsilsesquioxane, dimethicone/vinyldimethicone crosspolymer, dimethicone/bis-isobutyl PPG-20 crosspolymer, dimethicone crosspolymer, mica, silica, nylon-12, poly (methyl methacrylate), boron nitride, polyethylene, hexamethylene diisocyanate/trimethylol hexyllactone crosspolymer, magnesium stearate, zinc oxide, and mixtures thereof.

8. The cosmetic preparation as set forth in claim 1, wherein the preparation is shaped into a stick.

9. The cosmetic preparation as set forth in claim 1, wherein the preparation is a cosmetic preparation selected from the group consisting of: eyeliner, eyeshadow, eyebrow pencil, tattoo, lipliner, lipstick, mascara, blusher, or concealing material.

10. The cosmetic preparation as set forth in claim 1, wherein one of the at least two volatile components is isododecane and a second volatile component consists of a mixture of (1) hydrogenated polyisobutene, (2) hydrogenated polydecene and (3) hydrogenated poly(C6-14 olefins).

11. The composition of claim 1, wherein the at least one silsesquioxane wax is present in an amount between 1 and 20% by weight, and wherein the hydrogenated polydicyclopentadiene is present in an amount between 2 and 20% by weight.

\* \* \* \* \*